United States Patent [19]
Brehier

[11] Patent Number: 5,383,924
[45] Date of Patent: Jan. 24, 1995

[54] EXTRACTABLE CARDIAC PROBE AND ITS APPLICATION PROCEDURE

[75] Inventor: Jacques Brehier, Le Mans, France

[73] Assignee: Ela Medical, Montrouge Cedex, France

[21] Appl. No.: 71,675

[22] Filed: Jun. 3, 1993

[30] Foreign Application Priority Data

Jun. 3, 1992 [FR] France ................... 92 06704

[51] Int. Cl.6 ................................ A61N 1/05
[52] U.S. Cl. ................................ 607/126
[58] Field of Search ............ 607/115, 116, 119, 120, 607/122, 125–132; 128/642

[56] References Cited

U.S. PATENT DOCUMENTS 4,883,070 11/1989 Hanson ................... 607/116

FOREIGN PATENT DOCUMENTS 2099307 12/1982 United Kingdom ........... 607/126

Primary Examiner—Lee S. Cohen
Assistant Examiner—Jeffrey R. Jastrzab
Attorney, Agent, or Firm—Davis Hoxie Faithfull & Hapgood

[57] ABSTRACT

An extractable cardiac probe comprising a catheter (4) and a sleeve (3) that is at least partially deformable and mountable to the catheter. The procedure for application of the extractable probe uses an extractor device (11) equipped to pass between the sleeve and catheter to deform the sleeve (3) elastically to permit removal and replacement of the catheter.

42 Claims, 1 Drawing Sheet

EXTRACTABLE CARDIAC PROBE AND ITS APPLICATION PROCEDURE

FIELD OF THE INVENTION

The invention relates to an extractable cardiac probe and its application procedure.

BACKGROUND OF THE INVENTION

Cardiac probes are used for cardiac stimulation and to pick up electrical signals originating from the heart. A probe comprises two tips: one called proximal, which is, in the context of cardiac stimulation, intended to be connected to the signal generator; the other is called distal and is intended to be placed in contact with the cardiac muscle, e.g., the inner surface of the cardiac muscle.

The probe comprises an electrical conductor comprising a metal wire coiled in a spiral or helical manner and arranged inside a biocompatible flexible sheath made, for example, of silicone rubber. The conductor is connected to an electrode, e.g., a ring-shaped or cylindrical electrode, arranged at the distal tip of the probe.

Various incidents can occur on the occasion of use of cardiac probes. On the one hand, it is necessary to replace a probe which is not functioning correctly with a new probe. On the other hand, focuses of infection may break out at the tip or along the probe.

Extraction of the probe is imperative in the preceding cases. For this purpose, a known extraction procedure calls for pulling on the probe by applying a constant traction on the order of 1N to 5N until there is detachment of the probe from the surface of the cardiac muscle. This operation, which is long and arduous for the patient, often takes several days.

Documents DE 3,937,594, U.S. Pat. Nos. 4,574,800 and 4,988,347 describe three different devices for extraction of a cardiac probe, the common element of which is the following. These devices, expansible through enlargement of their outside diameter, are inserted inside the electrical conductor coiled in a spiral up to the vicinity of the distal tip of the probe. Then they are fastened to this distal tip by means of expansion of their outside diameter, so as to be able to exercise a traction on this distal tip. One drawback resulting from the use of these known devices is the risk of tearing of the fibrin surrounding the distal tip of the probe and, possibly, of a portion of the myocardium.

SUMMARY OF THE INVENTION

It is an object of the invention is to remedy the drawbacks of the known devices and procedures, by proposing an extractable cardiac probe, the application of which substantially reduces the risks of tearing of fibrin or a portion of the myocardium.

It is another object to provide an extractable probe that allows for a relatively rapid extraction of an implanted catheter and its reinsertion or replacement. It is another object to provide the same with reduced traction and minimal disturbance and trauma to the cardiac tissue and patient as compared to prior devices.

Broadly, the present invention is directed to an extractable cardiac probe, specifically for use with a cardiac stimulator, of the type comprising a catheter with a flexible sheath, having an electrode at its distal tip that is intended to be placed against an inner surface of the heart, and an appreciably cylindrical sleeve having an internal diameter which engages the catheter at the catheter distal end and containing means for attaching the probe to the cardiac surface, said catheter being able to be disunited (separated) from said sleeve to permit the withdrawal of the catheter from the sleeve and to permit the retention of the sleeve in place on the cardiac surface, characterized in that said sleeve is at least partially deformable by expansion of the diameter of its internal passage to allow the extraction of the catheter by sliding movement.

In a preferred embodiment, the probe comprises, on the side of the sleeve turned toward its proximal tip, a part that is shaped for the introduction of a separator device between the sleeve and the catheter. The continued advancement of the separator device toward the distal end will deform the sleeve inner surface away from the catheter and thus expand the internal passage. The part may be any shape that, at the proximal end of the sleeve, permits the separator device to pass between the sleeve and the catheter to expand the inner diameter of the sleeve. One such suitable shaped part is an appreciably cylindrical part adapted to accept a tubular separating implement. One such appreciably cylindrical part may be a frustroconical section, having a wider diameter at the proximal end than at the distal end. The proximal end of the sleeve either may be spaced a distance from the catheter to permit passing the separator device under the sleeve, or may comprise a beveled face that is urged outwardly by the advancing separator device.

Preferably, the sleeve and the catheter also comprise cooperating interlocking shapes along opposing surfaces, for lockingly engaging the sleeve to the catheter when the sleeve is mounted on the catheter for use. Such interlocking shapes may be, e.g., grooves interacting with retention rings, or bosses interacting with recesses, that cooperate to lock together integrally the sleeve and the catheter to prevent relative movement. The shapes may be located with the male or protruding surfaces on either the sleeve inner surface or on the catheter, with the corresponding female or recessed surface located on the opposing surface.

The sleeve also preferably comprises an appreciably non-deformable component at its distal tip, for example, a retention ring which may be made of a radiopaque material.

The catheter preferably comprises, in the vicinity of its distal tip, a retention insert fastened to the flexible sheath, e.g., by gluing or bonding or by friction. The retention insert may be a tube made of a radiopaque material. The retention insert may interact with a portion of the interlocking shape on the sleeve inner surface for locking the sleeve in position at the distal end of the catheter.

Another aspect of the invention is directed to a procedure for application of an extractable probe characterized by the following steps:

(1) placing a separator device around the probe catheter and causing it to move toward the distal tip of the probe, e.g., over and along the proximal tip to the distal tip;

(2) introducing the separator device between the sleeve and the catheter to deform the sleeve elastically and to increase the inside through-pass diameter of the sleeve; and (3) withdrawing the catheter by traction through the sleeve and the separator.

The separator device may be advanced until it abuts the non-deformable component when it is fully inserted.

In a preferred embodiment, the method is further characterized by the step of inserting a new catheter following extraction of the old catheter. The insertion procedure preferably comprises the steps of:

(4) leaving the sleeve in place after withdrawal of the catheter;

(5) holding the sleeve in position with the aid of the separator device, so as to maintain the through-pass diameter corresponding to the outside diameter of the catheter;

(6) inserting a new catheter through the separator and the sleeve to the surface of the myocardium; and (7) withdrawing the separator, leaving in place the catheter made integral, e.g., interlockingly engaged, with the sleeve following elastic reversion of the sleeve on the catheter.

BRIEF DESCRIPTION OF THE DRAWINGS

The invention shall be better understood with the aid of the following detailed description of the invention, presented by way of a non-restrictive example, and with reference to the attached drawings, in which like reference numerals refer to like elements and in which.

DETAILED DESCRIPTION OF THE INVENTION

Figure 1:
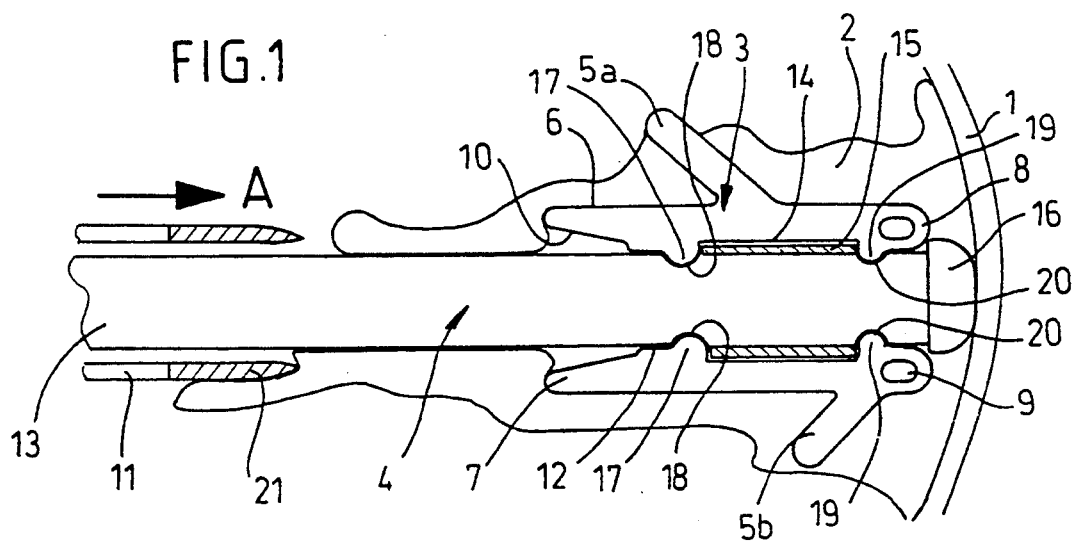
FIG. 1 represents a schematic sectional view of an extractable probe in accordance with an embodiment of the present invention, attached to the myocardium in position for use.

With reference to FIG. 1, a probe in accordance with the invention is shown in which the distal tip end, which is surrounded by fibrin 2, has been implanted on the surface 1 of the cardiac muscle. The probe in accordance with the invention is comprised of a sleeve 3 for implantation and retention, and a catheter 4.

The sleeve 3 comprises one or more flexible retention burrs 5a, 5b (also know as tines), projecting outward with respect to the external surface 6 of the appreciably cylindrical sleeve, in contact with the fibrin 2. The number of burrs is a design choice, although three burrs are suitable. The sleeve 3 is deformable at its proximal tip 7, and is reinforced at its distal tip 8 by an appreciably non-deformable component 9. Component 9 preferably is ring-shaped, made of metal or a radiopaque material, for example platinum-iridium.

The deformable tip 7 comprises internally an appreciably cylindrical first part 10 turned toward the proximal tip of the probe so as to permit the introduction of a tubular separator device 11 advancing along the probe in the direction of the arrow A to disengage the fibrin therefrom. First part 10 is an angled surface that at the most proximal location is spaced a distance from the outer surface of catheter 4. First part 10 is preferably a frustroconical section, but may be any suitable shape.

The cylindrical part 10 is extended continuously by an appreciably cylindrical part 12 with a diameter corresponding to the diameter of the flexible sheath 13 of the catheter, which is extended by another appreciably cylindrical part 14 with a greater diameter adapted to a retention insert 15 or other lug, preferably of radiopaque material.

The insert 15 is integral with the flexible sheath 13 and is advantageously made up of a metal tube enclosing the flexible sheath 13 in the vicinity of the electrode 16 of the catheter 4.

In accordance with one embodiment of the invention, the probe sleeve 3 and catheter 4 are equipped to be joined together prior to implantation, and to remain integral in position for cardiac stimulation by means of interacting shapes 17 and 18, 19 and 20, which are elastically deformable, preferably at least on the sleeve side.

The aforementioned joining of the catheter 4 to the inside of the sleeve 3, which in turn is or becomes anchored in the fibrin growth 2 by means of the burrs 5a, 5b, thus achieves the anchoring of the probe in the fibrin 2. This results in the secure attachment to the cardiac muscle 1, and permits stimulation of the latter.

The interacting shapes 17 and 18, 19 and 20, for example, arranged recessed on the sheath 13 and in relief on the sleeve 3, are preferably directly built in at the time of manufacture of the sleeve 3 and the sheath 13, of biocompatible material, for example, of the silicone-rubber type.

The interacting shapes 17 and 18, 19 and 20 are, for example, made up of rings projecting inward and corresponding retention grooves. In an alternate embodiment, the shapes may be made up of bosses in relief 17, 19 and recesses 18, 20 adapted to receive said corresponding bosses. It also is possible to provide only the shapes in relief 17, 19 on the sleeve, such that the flexible sheath of the catheter is deformed elastically to accommodate these forms. Such a structure results in the sleeve inner surface being compressed against the catheter outer sheath with sufficient pressure to maintain the catheter and sleeve lockingly engaged.

In accordance with the present invention, the insertion of a tubular separating device 11 disengages the fibrin at the proximal end of sleeve 3 and deforms the sleeve 3 sufficiently by enlarging its inside through-pass diameter to disunite the interacting forms 17 and 18, 19 and 20. This permits the extraction of the catheter 4 through a moderate traction effort corresponding to the disengagement of the electrode 16 from the surface 1 of the myocardium. This moderate traction is substantially less than the traction typically required to remove prior art devices, and is less than about 1N.

Figure 2:
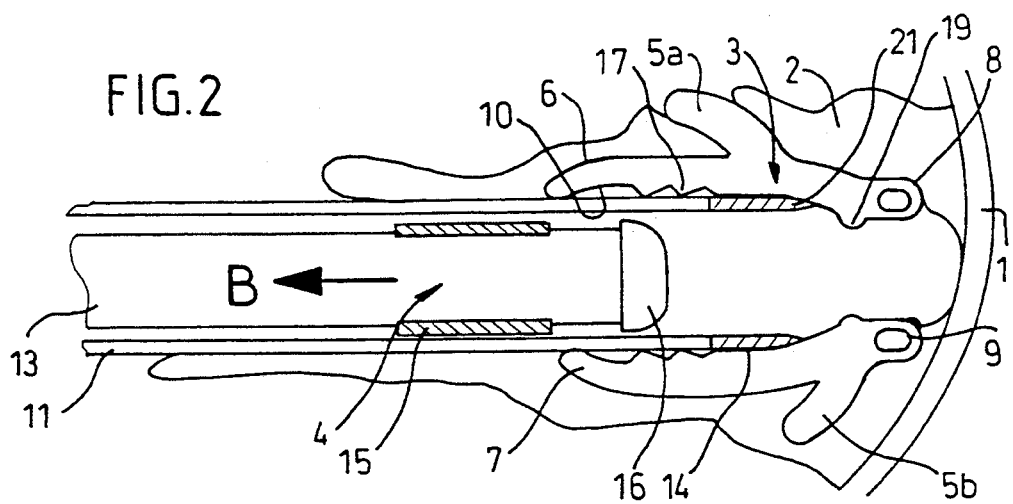
FIG. 2 represents a schematic sectional view of the extractable probe of FIG. 1, in which the electrode is in the process of extraction.

With reference to FIG. 2, the separator device 11 has been inserted at least up to the cylindrical part 14 of the sleeve 3.

The separator device 11, advantageously made up of a cylindrical sheath at the tapered, radiopaque tip 21, has an inside diameter that is sufficiently large to pass, with some clearance, the sliding outer surface of the sheath 13, the insert 15 and the electrode 16. The separator device 11 also advantageously has an outside diameter less than the diameter of the opening of the cylindrical tip 10 and greater than that of the cylindrical part 14, so as to appreciably increase the through-pass diameter on the inside of the sleeve 3, with the aid of insertion of the separator device 11 into the sleeve 3, and to permit the free sliding with clearance of the catheter 4 in the separator device 11. However, the outside diameter of the separator device is not large enough to cause the fibrin 2 at the distal end of the sleeve 3 to be disturbed or torn when the sleeve 3 inner diameter is enlarged.

After this insertion of the separator device 11 into the sleeve 3, the catheter 4, including the flexible sheath 13, the insert 15 and the electrode 16, is withdrawn by means of a moderate traction effort in the direction of the arrow B.

Figure 3:
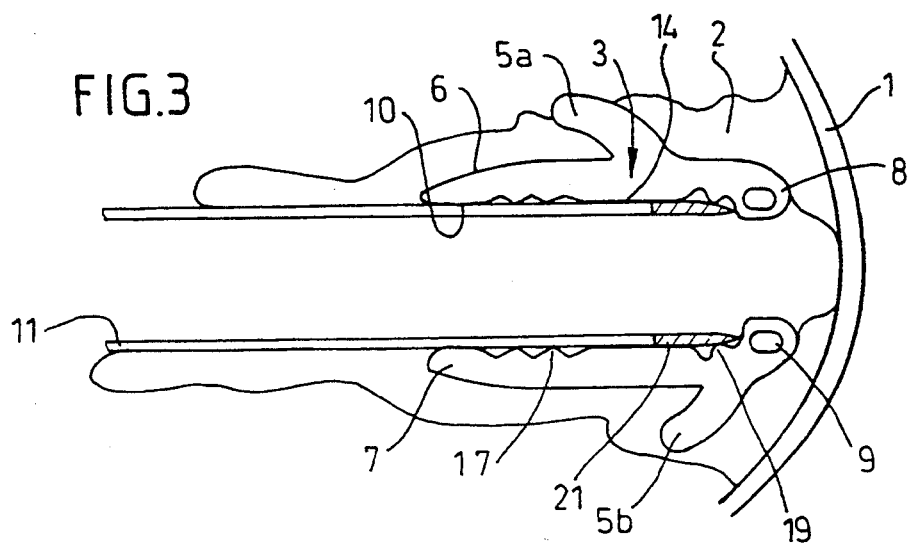
FIG. 3 represents a schematic sectional view of the probe sleeve of FIG. 1, in accordance with the invention, in an expanded position.

At the time of withdrawal of the catheter 4, the effort to be exerted corresponds to the detachment relating to the sleeve 3 and catheter 4 or to the passage of the electrode 16 under the bosses in relief 19. The separator device 11 may be supported in the sleeve 3 with the distal tip lodged against the portion of sleeve 3 containing the ring 9, as shown in FIG. 3. Thus the effort to be exerted to disunite the sleeve 3 from the catheter 4 involves only the separator device and the probe, without any significant traction or pressure on the cardiac surface 1 or the fibrin 2 resulting therefrom.

Withdrawal of the catheter 4 is thus accomplished without damaging specifically the bulk of the fibrin 2 or the surface 1 of the myocardium, leaving the sleeve 3 in place in the fibrin 2.

The corresponding stages of insertion of the probe, insertion of the separator device, and extraction of the catheter (and reinsertion of another catheter and withdrawal of the separator) are advantageously monitored by X-ray observation of the relative positions of the radiopaque parts 9, 15, 21.

With reference to FIG. 3, after having achieved the withdrawal of the catheter 4, one can intervene directly on the surface 1 of the myocardium to observe, take specimens for purposes of analysis, perform a surgical operation, e.g., remove the sleeve 3 by severing the fibrin, or disinfect said surface 1 by addition of antibiotics or other local medications, e.g., using a second catheter which is not limited to a cardiac catheter for stimulating the myocardium. Hence, some medical procedure can be performed at this stage.

Advantageously, with the aid of the present invention, the catheter 4 also may be reinserted or replaced with a new catheter, without damaging the surface 1 of the myocardium or the fibrin 2. This is because the elastically deformable sleeve 3 remains in place during this operation. After insertion of the new catheter 4, the separator device 11 is withdrawn. The sleeve 3 then resumes its initial form through elastic reversion, and becomes integral, i.e., interlocked, with the catheter 4.

One skilled in the art will appreciate that the present invention can be practiced by other than the described embodiments which are presented for purposes of illustration and not of limitation.

I claim:

1. An extractable cardiac probe for cardiac stimulation, comprising:
   a catheter having a proximal tip, a distal tip, and having a flexible outer sheath, and an electrode at the distal tip adapted to be placed against an inner surface of a heart; and
   a sleeve surrounding said catheter having a proximal tip, a distal tip, and means for attachment of the probe to a cardiac surface,
   said catheter being separable from said sleeve to permit the withdrawal of the catheter and the retention in position of the sleeve on the cardiac surface, wherein said sleeve has an inside diameter that securely engages the catheter, the sleeve being at least partially deformable through enlargement of the inside diameter to permit separation of the catheter and the sleeve and extraction of the catheter from the sleeve by sliding movement.

2. The probe in accordance with claim 1, wherein the sleeve proximal tip further comprises a shaped part to receive a separator device.

3. The probe in accordance with claim 2, wherein the shaped part is an appreciably cylindrical part having a proximal end adapted to receive a tubular separating device between the sleeve and the catheter.

4. The probe in accordance with claim 2 wherein the sleeve inside diameter and the catheter further comprise respective interacting shapes so that the sleeve and catheter interlock to securely attach to one another.

5. The probe in accordance with claim 4 wherein the respective interacting shapes further comprise a groove interacting with a retention ring.

6. The probe in accordance with claim 4 wherein the respective interacting shapes further comprise a boss interacting with a recess.

7. The probe in accordance with claim 4 wherein the sleeve further comprises an appreciably non-deformable component at its distal tip.

8. The probe in accordance with claim 7 wherein the non-deformable component is a retention ring of a radiopaque material.

9. The probe in accordance with claim 2 wherein the catheter further comprises, in the vicinity of its distal tip, a retention insert attached to the flexible sheath.

10. The probe in accordance with claim 9 wherein the retention insert is a tube of a radiopaque material.

11. The probe in accordance with claim 2 wherein the shaped part further comprises a frustroconical section having proximal and distal ends, the proximal end having a larger diameter than the distal end.

12. The probe in accordance with claim 1 wherein the sleeve inside diameter and the catheter further comprise respective interacting shapes so that the sleeve and catheter lockingly engage one another.

13. The probe in accordance with claim 12 wherein the respective interacting shapes further comprise a groove interacting with a retention ring.

14. The probe in accordance with claim 12 wherein the respective interacting shapes further comprise a boss interacting with a recess.

15. The probe in accordance with claim 1, wherein the sleeve further comprises an appreciably non-deformable component at its distal tip.

16. The probe in accordance with claim 15, wherein said non-deformable component is a retention ring of radiopaque material.

17. The probe in accordance with claim 1, wherein the catheter comprises, in the vicinity of its distal tip, a retention insert attached to the flexible sheath (13).

18. The probe in accordance with claim 17, wherein said retention insert is a tube of radiopaque material.

19. An extractable probe system for providing a replaceable cardiac stimulation catheter for stimulating cardiac tissue comprising:
   a catheter having a proximal end, a distal end, an electrode at the distal end, and a flexible outer sheath, the outer sheath having a first surface area at the distal end and a maximum outer diameter; and
   a sleeve having a retention burr and an elasticly deformable inner surface, the inner surface having a rest condition and an expanded condition, the sleeve being selectively mounted on the catheter so that the inner surface in the rest condition engages at least a portion of the first surface area of the catheter and the retention burr will maintain the electrode in contact with cardiac tissue, and so that the inner surface in the expanded condition has an inner diameter that is larger than the maximum outer diameter of the catheter, whereby the catheter may be removed from the sleeve by sliding movement.

20. The system of claim 19 wherein the sleeve inner surface further comprises a projection and wherein the catheter distal end further comprises a retention element, the projection being spaced on the catheter proximal end side of the retention element when the sleeve inner surface is engaged with the catheter first surface area.

21. The system of claim 20 wherein the sleeve further comprises a distal end and a retention ring at the distal end.

22. The system of claim 21 wherein the sleeve retention ring and the catheter retention element each further comprise a radiopaque material.

23. The system of claim 19 wherein the portion of the first surface area and the sleeve inner surface further comprise interlocking complementary shapes.

24. The system of claim 23 wherein the interlocking complementary shapes comprise a boss and a recess, one of which is in the first surface area and the other of which is in the sleeve inner surface.

25. The system of claim 23 wherein the interlocking complementary shapes comprise a groove and a retention ring, one of which is in the first surface area and the other of which is in the sleeve inner surface.

26. The system of claim 19 further comprising a separating element about said catheter having a distal tip and an inner diameter, the inner diameter being dimensioned to permit the separating element to slide along the catheter and the distal tip being dimensioned to pass between the sleeve and the catheter as the separating element is passed along the catheter, thereby to place the sleeve inner surface in the expanded condition.

27. The system of claim 26 wherein the sleeve inner surface further comprises a projection and wherein the catheter distal end further comprises a retention element, the projection being spaced on the catheter proximal end side of the retention element when the sleeve inner surface is engaged with the catheter first surface area.

28. The system of claim 27 wherein the sleeve further comprises a distal end and a retention ring at the distal end.

29. The system of claim 28 wherein the separating element distal tip further comprises a ring of radiopaque material, and wherein the sleeve retention ring and the catheter retention element each further comprise a radiopaque material.

30. The system of claim 26 wherein the portion of the first surface area and the sleeve inner surface in the rest condition further comprise complementary shapes biased in interlocking contact.

31. The system of claim 30 wherein the interlocking complementary shapes comprise a boss and a recess, one of which is in the first surface area and the other of which is in the sleeve inner surface.

32. The system of claim 30 wherein the interlocking complementary shapes comprise a groove and a retention ring, one of which is in the first surface area and the other of which is in the sleeve inner surface.

33. A method of providing a probe for use in stimulating cardiac tissue comprising the steps of:
(a) providing a catheter with a flexible outer sheath having a maximum outer diameter, a distal end, a proximal end, an electrode at the distal end for contacting cardiac tissue, and a first contacting surface located near the distal end proximal of the electrode;
(b) providing a sleeve with an inner surface and an outer surface, the outer surface having at least one retention burr projecting outwardly, the inner surface being deformable and having a rest condition and an expanded condition, the expanded condition having an inner diameter that is greater than the maximum outer diameter of the catheter outer sheath;
(c) mounting the sleeve over the catheter with the sleeve inner surface in the rest condition in locking engagement with the catheter first surface; and
(d) positioning the mounted sleeve and catheter so that the catheter electrode is in touching contact with the cardiac tissue to be stimulated and maintaining the electrode in said position for a time sufficient to permit fibrin to grow over the retention burr, thereby to secure the catheter electrode in place.

34. The method of claim 33 wherein step (b) further comprises providing the sleeve inner surface with a proximal end having a diameter that is greater than the maximum outer diameter of the catheter in the rest condition.

35. The method of claim 33 further comprising:
(e) providing a separator having a distal tip and an inner diameter passageway that is greater than the maximum outer diameter of the catheter outer sheath;
(f) placing the separator around the catheter and sliding the separator along the catheter so that the separator distal tip passes between the sleeve inner surface and the first surface of the catheter, thereby placing the inner surface in the expanded condition; and
(g) removing the catheter from contact with the cardiac tissue using traction so that the separating device remains in contact with the sleeve inner surface and the sleeve remains in contact with the grown fibrin.

36. The method of claim 35 wherein step (g) further comprises applying a traction force that is less than about 1 Newton.

37. The method of claim 35 further comprising the step of inserting a second catheter proximate to the cardiac tissue by passing it through the inner passageway of the separator.

38. The method of claim 37 wherein the inserting step further comprises inserting a second catheter other than a cardiac stimulating catheter for performing a medical procedure other than cardiac stimulation.

39. The method of claim 37 wherein the inserting step further comprises inserting a cardiac stimulating catheter having a first surface area and an electrode so that the electrode is in touching contact with the cardiac tissue to be stimulated, and removing the separator by sliding along the second catheter so that the sleeve inner surface returns to its rest condition and lockingly engages the first surface area of the second catheter.

40. A probe for providing stimulating pulses to cardiac tissue comprising:
a catheter having a flexible outer sheath, a distal end, and an electrode at the distal end;
a sleeve having an outer surface on which fibrin may develop and a deformable elastic inner surface, the sleeve being mounted on the catheter with at least a portion of the deformable elastic inner surface frictionally engaged with a portion of the catheter outer sheath, wherein the sleeve deformable elastic inner surface is enlargeable to a diameter that will permit extraction of the catheter by sliding.

41. The probe of claim 40 wherein the sleeve inner surface has a proximal end and a distal end, and the proximal end has an outer diameter that is greater than the flexible outer sheath.

42. The probe of claim 40 wherein the sleeve inner surface has a first shape and the catheter sheath has a second shape opposite the first shape when the sleeve is mounted on the catheter, the first and second shapes providing locking engagement between the catheter and the sheath.

* * * * *